United States Patent [19]

Grady et al.

[11] Patent Number: 4,896,344
[45] Date of Patent: * Jan. 23, 1990

[54] X-RAY VIDEO SYSTEM

[76] Inventors: John K. Grady, 111 Slough Rd., Harvard, Mass. 01451; Richard E. Rice, 243 Lowell St., Arlington, Mass. 02174

[*] Notice: The portion of the term of this patent subsequent to Aug. 6, 2002 has been disclaimed.

[21] Appl. No.: 661,146

[22] Filed: Oct. 15, 1984

[51] Int. Cl.⁴ .............................................. H05G 1/64
[52] U.S. Cl. ..................................... 378/99; 378/146; 358/111
[58] Field of Search .................... 358/111; 378/99, 146

[56] References Cited
U.S. PATENT DOCUMENTS

| | | | |
|---|---|---|---|
| 3,758,723 | 9/1973 | Green et al. | 358/111 |
| 3,790,785 | 2/1974 | Paolini et al. | 378/99 |
| 4,164,657 | 8/1979 | Duniker et al. | 358/111 |
| 4,185,198 | 1/1980 | Fujimoto | 378/99 |
| 4,203,037 | 5/1980 | Gur et al. | 378/37 |
| 4,315,146 | 2/1982 | Rudin | 378/146 |
| 4,355,331 | 10/1982 | Georges | 358/111 |
| 4,404,591 | 9/1983 | Bonar | 358/111 |
| 4,504,859 | 3/1985 | Grady et al. | 378/99 |
| 4,534,051 | 8/1985 | Grady et al. | 358/111 |
| 4,581,753 | 4/1986 | Rice | 378/99 |

OTHER PUBLICATIONS

Varian, VII-116 Zoom Image Intensifier, LSE Divisio, 601 California Ave., Palo Alto, California 94303. undated.
Heintzen, P. H. and Brennecke, P. *Digital Imaging in Cardiovascular Radiology*, Thieme-Stratton Inc. N.Y. (1983) pp. 41-56.
Nelson, R. S. et al. "An evaluation of a fluorescent screen-isocon camera system for x-ray imaging in radiology", Med. Phys. 9(5), Sep./Oct. 1982, 777-783.

Primary Examiner—Carolyn E. Fields
Assistant Examiner—David P. Porta
Attorney, Agent, or Firm—James H. Grover

[57] ABSTRACT

In an X-ray system in which a source directs X-radiation through a subject to a receptor which produces a secondary planar light image, the light image is projected on the planar input face of a light intensifier after passing through the scanning aperture of a moving mask substantially at the plane of the projected light image. Preferably the system includes a moving X-ray mask with a scanning aperture between the source and receptor and means driving the X-ray and light masks in synchronism with their apertures optically superimposed.

22 Claims, 2 Drawing Sheets

X-RAY VIDEO SYSTEM

BACKGROUND OF THE INVENTION

The present invention involves X-ray systems in which a beam of X-ray energy modified by passing through a subject is converted to electrical video signals suitable for display or recording, with or without computer processing, to allow visual evaluation. Conversion of X-ray patterns is currently accomplished by X-ray image intensifiers which in one tube combines an internal receptor of the X-radiation, typically an X-ray responsive scintillation screen producing a corresponding secondary, light image with electronic amplification. The prior internal screen, X-ray image intensifier, however, introduces degradation of the X-ray and light images which is becoming less acceptable, particularly in video displayed, digitally processed radiography. An X-ray image intensifier tube has the inherent disadvantage in that its internal scintillation screen does not allow baking the photocathode sufficiently for optimum evacuation of cathode contaminants. Consequently electrons are unduly scattered from the photocathode rather than focussed on the scintillation screen, and along with the other causes, produces an unwanted veiling glare throughout the screen area which radically reduces the signal-to-noise ratio and contrast in the light output of the X-ray image intensifier.

An alternative system comprises an X-ray responsive scintillation screen receiving the X-ray pattern directly and producing a secondary light image on a screen from which it can be projected to a light receiver. Hitherto known systems, however, lack the quality of projection optics to meet the fine resolution of X-ray detail of which current video signal processors are capable.

The disparity between the resolution capability of an X-ray system and that of a video processor can be reduced by using known radio-opaque and light-opaque scanning masks which considerably reduce scattered X-rays and background fog or glare and the like in the light image and consequent noise and poor definition in the corresponding video signal.

It is one object of the present invention further to improve efficiency of light amplification in an X-ray system to provide brighter video images of higher quality than prior systems and in which image degradation caused by X-ray scatter and veiling glare is reduced as compared to systems using an X-ray image intensifier with an internal X-ray responsive screen. Further objects are to provide an X-ray system which provides more efficient control in the gain in light amplification, which allows radiation of variable areas of a subject, and which compactly supports the light receptor portion of the system.

SUMMARY OF THE INVENTION

According to the invention an X-ray system for radiological examination of a subject comprises an X-ray source directing radiation on a path through a subject position; an X-ray receptor on the path beyond the subject position responsive to X-radiation to produce a secondary, planor light image; optical means projecting the secondary image on a light path; and a light intensifier beyond the optical means for amplifying the intensity of the light image; wherein the intensifier has a planar input face receiving a planar projected light image, and the system includes a moving light mask between the receptor and intensifier with an image scanning aperture substantially at the plane of the projected light image.

Preferably the image intensifier tube includes a light input area and a light output area coupled to the camera tube, and a zoom control adjustable to magnify the image at the input area so as substantially to fill the output area. The system may have a moving radio-opaque mask between the X-ray source and receptor for reducing X-ray scatter from the subject. An additional moving mask between the optical means and light receptor reduces light scatter to the light receptor resulting from X-ray scatter. Folding the optical path through the optical means relative to the X-radiation path accommodates the length of the video camera tube.

DRAWINGS

DESCRIPTION

Figure 1:
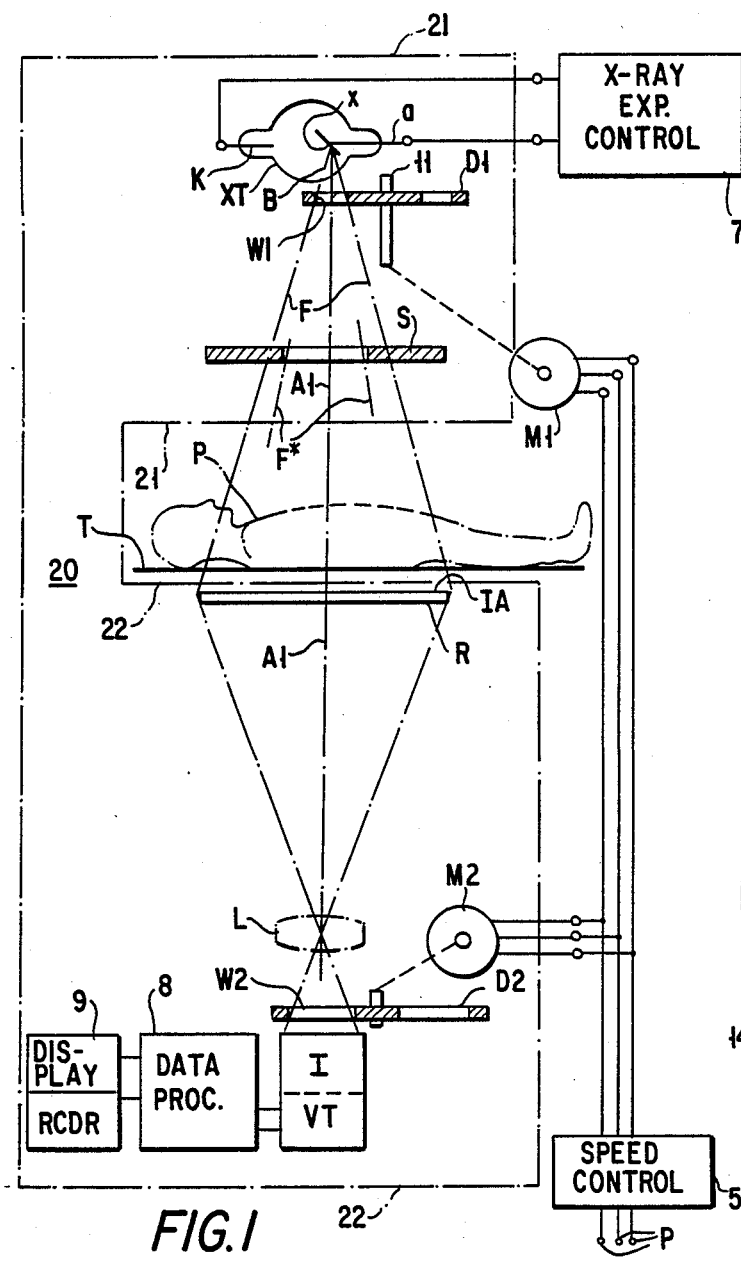
FIG. 1 is a general schematic view of X-ray apparatus with moving masks and a video system according to the invention.
Figure 2:
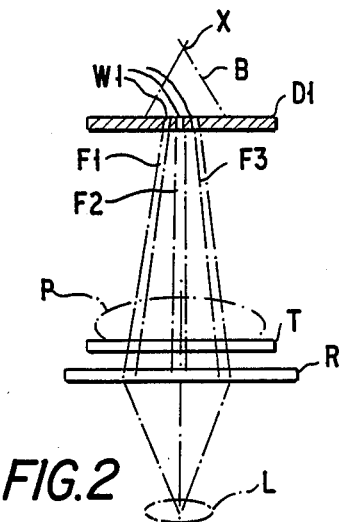
FIG. 2 is a schematic showing of part of the apparatus at right angles to the view of FIG. 3.

In the X-ray system of FIGS. 1 and 2 the X-radiation source is the focal spot X on the anode a of an X-ray tube XT. The X-ray tube XT is energized by an electronic X-ray exposure control 7. From the source X a pyramidal or conical beam B is radiated on a radiation axis A1 toward the position P of a subject such as a human patient on an X-ray transmissive support table T. Beyond the patient position P is an X-ray receptor R having an X-ray responsive imaging area or plane IA. Typically the receptor is a scintillation screen emitting visible light secondary radiation on receipt of X-rays. The area of the patient exposed to radiation may be varied by a collimator S which will vary the exposed area of the receptor producing the secondarily emitted light image. The variable area secondary image at the area IA is viewed on the axis A1 by an electro-optical video system described in detail hereinafter, and including a lens L, a light image intensifier I and a video camera tube VT, which converts the secondary image into a frame of electrical video signals corresponding to the subject under examination. The video signals are transmitted through a digital data processor 8 to a display or recorder 9. Currently video processors and displays are capable of resolving as many as 150 visually useful tone shades in an X-ray image and such fine tone gradation is important to accurate medical diagnosis, but the scatter of X-rays from a human patient degrades the image below such resolution unless radiation masks are used.

Figure 3:
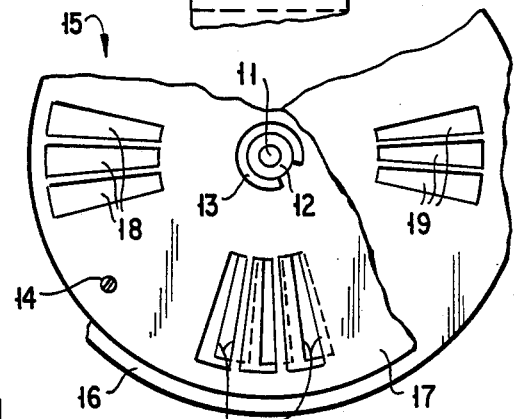
FIG. 3 is a plan view of the moving mask of FIGS. 1 and 2.

The X-ray beam B is partially intercepted by an X-ray opaque mask comprising a first rotating disk D1 having X-ray transmissive slits or windows W1. As shown in FIG. 3 the windows W1 are sectoral and will transmit a fan-shaped scanning X-ray beam F while the disk D1 masks the remainder of the conical beam B from the receptor R. The windows might, however, be parallel sided rectangular slits in a belt moving linearly or reciprocating through the X-ray beam B. A second, light mask D2 with like windows W2 is located between a lens L and video tube VT. The disks D1 and D2 are rotated in phase by synchronous motors M1 and M2 respectively. As shown in FIG. 2 the windows W1 and W2 of the disks are optically superimposed so that, as the first disk mask D1 is synchronously driven by connection through a speed control 5 to clock regulated alternating current power terminals p, the second disk windows W2 scans the secondary image area IA substantially simultaneously with the scanning of the same area by the first disk windows W1.

Shown in FIG. 3 is a composite disk 15 which preferably is substituted, in the appropriate size, for the disks D1 and D2 of FIGS. 1 and 2. The composite disk 15 comprises two superimposed disks 16 and 17, one disk 16 being secured to the shaft 11 driven by the motor M1, and one disk 17 having a sleeve 12 rotatably secured on the shaft by a retainer ring 13. While the one disk 17 may be rotated relative to the other disk, the two disks are normally locked to each other by a set screw 14 threaded through one disk 16 and engaging the other against relative movement. The respective disks 16 and 17 each have, for example, four sets of sectoral windows 18 and 19 which include an angle of a few degrees, each set including from a few to nearly ninety degrees. The windows of both disks overlap to define smaller sectoral X-ray windows W1* opening through both disks and adjustable in width by relative rotation of the disks 16 and 17.

Figure 5:
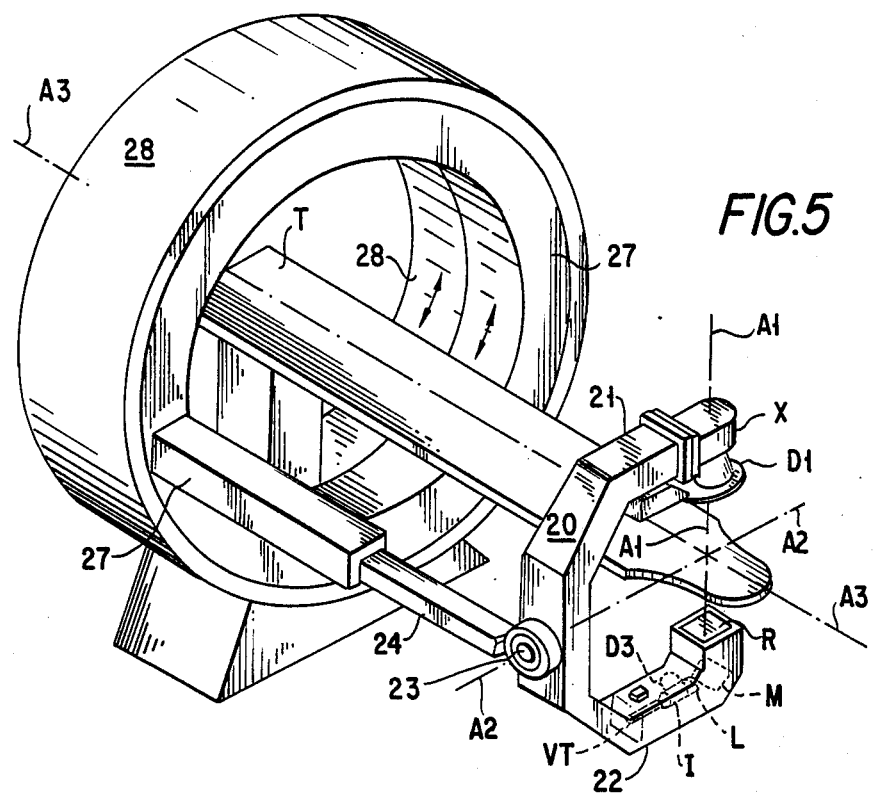
FIG. 5 is an isometric view of an X-ray stand including the video system of FIG. 4.
Figure 6:
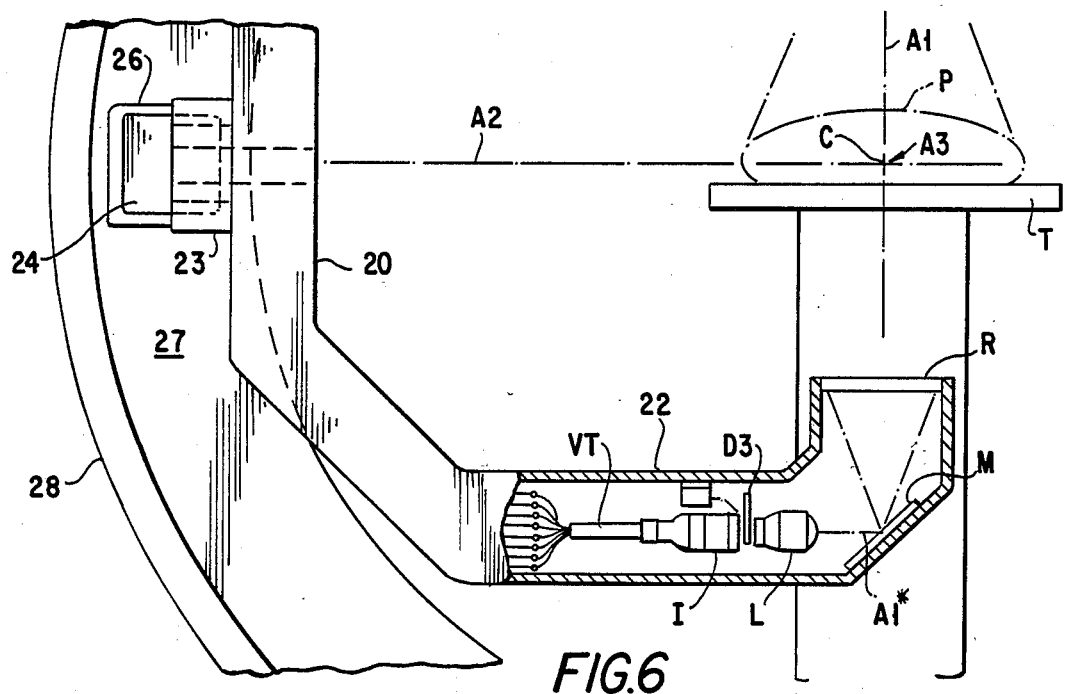
FIG. 6 is a fragmentary end view of the stand.

The X-ray tube XT and masking disk D1 are carried on one arm 21 of a two-armed support 20, while the X-ray receptor R, lens L, second, light masking disk D2, light image intensifier I and camera tube VT are carried on a second arm 22 of the support 20 as shown diagrammatically in FIG. 1 and structurally in FIGS. 5 and 6.

As shown in FIGS. 5 and 6 the two-armed support 20 is pivoted on an axis A2 by a bearing 23 held on a beam 24 which slides telescopingly in a sleeve 26. The sleeve is mounted on a first ring 27 which rotates on an axis A3 within a circular frame 28 with a base 29. A second ring 31 rotating in the frame 28 on the same axis A3 supports the patient table T.

Figure 4:
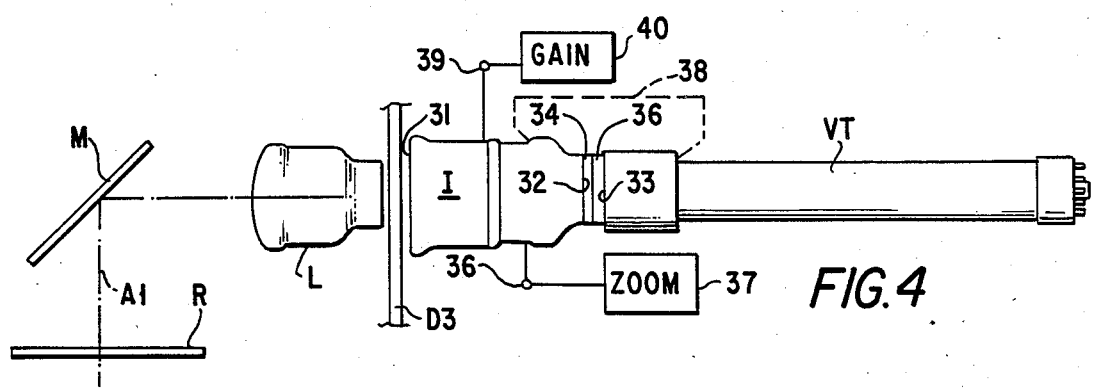
FIG. 4 is an enlarged side view of the video system of FIG. 1.

According to the present invention the second arm 22 supports a novel video system employing a light image intensifier (as contrasted to the prior X-ray image intensifier) in which the scintillation screen is spaced from the light intensifier by air or a like optical medium and the light path A1 between the X-ray receptor R and the light image intensifier tube is folded by a first-surface mirror M, the X-ray receptor being external of the light image intensifier tube. Part of the video system can therefore extend at right angles to axis A1 of the X-ray beam and light path along the second support arm 22, in contrast to prior X-ray systems in which the axis of the image intensifier coincided with the light path axis. Realigning the video system on an axis A1* at right angles to the radiation axis A1 greatly shortens the space between the X-ray tube arm 21 and the receptor arm 22. This space reduction may be architecturally mandatory in a hospital X-ray room. The limited height between ceiling and floor may be insufficient to allow for the assembled length of the video system, particularly when, as in the present invention, it includes a lens L, light masking disk D2, image intensifier I and camera tube VT, as shown in FIGS. 4, 5 and 6.

A further aspect of the invention involves the projection of the planar light image from an external X-ray receptor and secondary light radiator onto the planar image intensifier input face by the lens L. To achieve the resolution quality of the subsequent video system the area of the light image must be compatible geometrically with the image projected by the optical system and with the input face of the intensifier. For example, the image area IA and the input face 31 of the image intensifier tube I should be planar, and the projection optics Z should project from plane to plane without distortion, preferably with reduction in area.

A suitable, external X-ray receptor and secondary light radiator is the rear element of a pair of gadolinium oxysulfide ($Gd_2O_2S$) scintillation screens sold by Minnesota Mining and Manufacturing Company, St. Paul, Minn., under the name TRIMAX 12.

By way of example, the lens L has a focal length to aperture ratio (f-number) of 1, and a focal length of about 100 millimeters. Increasing the focal length of the lens greatly increases the distance between the receptor R and image intensifier I.

The image intensifier I is preferably a zoom image intensifier tube such as model VL1-116 of Varian Image Tube Division, Palo Alto, California. It has a planar input face area 31 and a fiber optic output face area 32. A zoom electrode 36 is connected to a zoom control 37 for varying magnification.

The video tube VT preferably is an image isocon camera tube such as type 4807 made by RCA Solid State Division of Lancaster, Pennsylvania. It has a fiber optic input face area 33.

The two fiber optic elements are optically coupled with an intermediate thin film of optical oil, and held in contact by a clamp 38, providing an interface of high optical efficiency.

The light intensifying combination of the image intensifier, closely coupled to the isocon tube significantly improves the light amplification and quality of the isocon video signal output in comparison with the output of the isocon system. A relative gain of 75 in light energy is possible, for example.

The image intensifier has a light intensity gain electrode 39 whose potential is varied by a gain control 40. Some X-ray examination procedures such as an angiography result in images whose light intensity as transmitted through the lens L and light image intensifier I would overload the isocon video tube VT unless reduced. To stop down the lens would reduce the light input to the video tube but at a sacrifice of the ratio of signal to noise. But reducing the gain of the light image intensifier I, as is possible in the present system, maximizes the signal-to-noise rario and results in a significantly improved video signal output from the isocon.

An additionally important improvement in video signal quality of the isocon camera tube VT arises from the ability of the image intensifier I to match its light output area 32 with the light input area 33 of the isocon VT. This matching can be accomplished by appropriate selection of the image intensifier and isocon. But additionally, if the image intensifier has the zoom capability of the Varian VL1-116 tube, the area matching can be achieved even if the area of secondary radiation on the scintillation screen X-ray receptor R is varied. As previously described a radio-opaque collimator S shown in FIG. 1 may be adjusted to reduce the area of the patient exposed to X-rays. In this case the area of the secondary image at the receptor R viewed by the lens L will also be reduced. Without zoom capability the image at the output face of the image intensifier would not fill the light output area 34 of the intensifier nor the light input area 35 of the isocon camera tube VT. Such area mismatch greatly reduces the efficiency of light usage. According to the present invention the image intensifier has a zoom electrode 36 and control 37 with the ability to vary the area of its output image. This makes it possible to produce a reduced area image at the image intensifier light input face 31 so as to fill the intensifier output face area 32 to match the isocon input face area 33. Although the image size could be restored electronically by stages subsequent to the isocon, image quality would be degraded in resolution and signal to noise ratio. Image size could also be restored by moving the lens, but this would involve moving the disk D2 and the intensifier-isocon assembly introducing difficult mechanical movements and tolerances avoided by use of the zoom intensifier to maintain constant image size at the isocon video tube input face 33.

It should be understood that the present disclosure is for the purpose of illustration only and that this invention includes all modifications and equivalents which fall within the scope of the appended claims.

We claim:

1. An X-ray system for radiological examination of a subject comprising:
   an X-ray source directing radiation on a path through a subject position;
   an X-ray scintillation screen on the path beyond the subject position responsive to X-radiation to produce a secondary, planar light image;
   optical means projecting the secondary image from the scintillation screen on a light path; and
   a light image intensifier tube beyond the optical means for amplifying the intensity of the light image; wherein
   the intensifier tube has a planar input face receiving a planar projected light image, and the system includes a movable light mask between the scintillation screen and intensifier tube with an image scanning aperture substantially at the plane of the projected light image.

2. An X-ray system according to claim 1 wherein the X-ray scintillation screen is external of and spaced from the intensifier tube.

3. An X-ray system according to claim 1 wherein the optical means reduces the area of the projected image with respect to the secondary image area.

4. An X-ray system according to claim 1 including a movable X-ray mask between the source and scintillation screen with at least one scanning aperture.

5. An X-ray system according to claim 4 including means driving the X-ray and light masks in synchronism.

6. An X-ray system according to claim 4 wherein the X-ray and light masks have a plurality of optically superimposed apertures.

7. An X-ray system according to claim 1 wherein the light intensifier tube includes a video camera tube.

8. An X-ray system according to claim 1 wherein the light intensifier tube includes a light intensifier tube optically coupled to a video camera tube.

9. An X-ray system according to claim 8 wherein the tubes are coupled by a coherent fibre optic interface.

10. An X-ray system according to claim 9 wherein the light intensifier tube has a zoom control.

11. An X-ray system according to claim 10 including an X-ray collimator between the source and scintillation screen for varying the receptor area exposed to X-rays.

12. An X-ray system according to claim 8 wherein the light intensifier tube has a gain control.

13. An X-ray system according to claim 1 including a video camera tube optically coupled to the light intensifier tube for converting the light energy into video signals.

14. An X-ray system according to claim 13 wherein the X-ray scintillation screen is external of the light image intensifier tube.

15. An X-ray system according to claim 13 wherein the light image intensifier tube has a light output area substantially matching the light input area of the camera tube.

16. An X-ray system according to claim 13 wherein the light image intensifier tube includes a light input area and a light output area coupled to the camera tube, and a zoom control adjustable to vary the magnification of the image at the input area so as substantially to fill the output area.

17. An X-ray system according to claim 16 including an X-ray collimator between the source and subject position with an adjustable aperture for varying the area of the subject position exposed to X-rays.

18. An X-ray system according to claim 13 including an X-ray collimator between the source and subject position with an adjustable aperture for varying the area of the subject position exposed to X-rays.

19. An X-ray system according to claim 13 including a movable radio-opaque mask between the X-ray source and X-ray scintillation screen.

20. An X-ray system according to claim 13 including a coherent fibre optic coupling between the light image intensifier tube and camera tube.

21. An X-ray system according to claim 13 wherein the light intensifier tube has a gain control varying the light input to the video camera tube.

22. An X-ray system according to claim 1 wherein the scintillation screen has an X-ray responsive light imaging area as large as the area of a human patient exposed to radiation.

* * * * *